United States Patent
Baader et al.

[11] Patent Number: 5,356,909
[45] Date of Patent: Oct. 18, 1994

[54] SUBSTITUTED PYRIDINE-2,4-DICARBOXYLIC ACID COMPOUNDS AND THE USE THEREOF AND MEDICAMENTS

[75] Inventors: Ekkehard Baader, Königstein/Taunus; Martin Bickel, Bad Homburg; Dietrich Brocks, Wiesbaden; Volkmar Günzler, Marburg-Cappel; Stephan Henke, Dexheim; Hartmut Hanauske-Abel, Dexheim, all of Fed. Rep. of Germany

[73] Assignee: Hoechst Aktiengesellschaft, Frankfurt am Main, Fed. Rep. of Germany

[21] Appl. No.: 903,749

[22] Filed: Jun. 25, 1992

Related U.S. Application Data

[62] Division of Ser. No. 606,451, Oct. 31, 1990, Pat. No. 5,143,926, which is a division of Ser. No. 164,406, Mar. 4, 1988, Pat. No. 5,004,748.

Foreign Application Priority Data

Mar. 7, 1987 [DE] Fed. Rep. of Germany ... P3707429.6

[51] Int. Cl.$^5$ .................... C07D 213/81; A61K 31/44
[52] U.S. Cl. ....................... 514/335; 514/332; 514/336; 514/343; 514/350; 514/352; 546/261; 546/262; 546/263; 546/281; 546/283; 546/284; 546/299; 546/309; 546/310
[58] Field of Search .......... 546/809, 310, 261, 262, 546/263, 281, 283, 284, 299; 514/352, 332, 335, 336, 343, 350

References Cited

U.S. PATENT DOCUMENTS

| | | | |
|---|---|---|---|
| 4,482,437 | 11/1984 | Toomey, Jr. | 204/74 |
| 4,717,727 | 1/1988 | Gunzler et al. | 514/354 |

FOREIGN PATENT DOCUMENTS

| | | | |
|---|---|---|---|
| 0353668 | 7/1989 | European Pat. Off. | 546/309 |
| 0409119 | 7/1990 | European Pat. Off. | 546/309 |
| 0414216 | 8/1990 | European Pat. Off. | 546/309 |
| 0430029 | 11/1990 | European Pat. Off. | 546/309 |
| A3432094 | 3/1986 | Fed. Rep. of Germany | 514/354 |
| A3703959 | 8/1988 | Fed. Rep. of Germany | 514/354 |
| A3703962 | 8/1988 | Fed. Rep. of Germany | 514/354 |
| A3703963 | 8/1988 | Fed. Rep. of Germany | 514/354 |

OTHER PUBLICATIONS

Heinisch et al., Heterocycles, vol. 26, No. 3, pp. 731–744 (1987).
Beilsteins Handbuch der Organischen Chemie, 4, Auflage, drittes und viertes Erganzungswerk, vol. 20, pp. 1655 and 1778 (1979).
Gunzler et al., Collagen and Rel. Research, vol. 3, p. 71 (1983).
Majamaa et al., Eur. J. Biochem., vol. 138, pp. 239–245 (1984).
Sugiyama et al., Bull. Chem. Soc. Japan, vol. 58, No. 4, pp. 1331–32 (1985).
Jones, J.A.C.S., vol. 73, pp. 5610–14 (1951).

*Primary Examiner*—C. Warren Ivy
*Assistant Examiner*—Zinna N. Davis
*Attorney, Agent, or Firm*—Finnegan, Henderson, Farabow, Garrett & Dunner

[57] ABSTRACT

The invention relates to substituted pyridine-2,4-dicarboxylic acid derivatives of the formula I

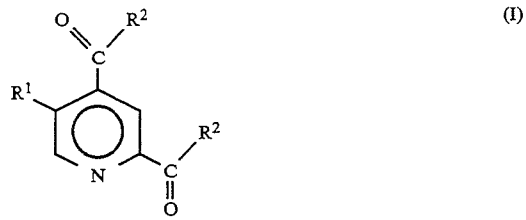

in which $R^1$ and $R^2$ have the meanings given. The invention also relates to a process for the preparation of the abovementioned compounds and to their use as medicaments, in particular as fibrosuppressants and immunosuppressants.

7 Claims, No Drawings

SUBSTITUTED PYRIDINE-2,4-DICARBOXYLIC ACID COMPOUNDS AND THE USE THEREOF AND MEDICAMENTS

This is a division of application Ser. No. 07/606,451, filed Oct. 31, 1990 now U.S. Pat. No. 5,143,926 which is a division of application Ser. No. 07/164,406, filed Mar. 4, 1988 now U.S. Pat. No. 5,004,748.

DESCRIPTION

Compounds which inhibit prolinehydroxylase and lysinehydroxylase effect very selective inhibition of collagen biosynthesis by influencing collagen-specific hydroxylation reactions. In the course thereof, protein-bonded proline or lysine is hydrolyzed by the enzymes prolinehydroxylase or lysinehydroxylase. If this reaction is suppressed by inhibitors, a hypohydroxylated collagen molecule which is not capable of functioning and can be released by the cells into the extracellular space in only a small amount is formed. The hypohydroxylated collagen furthermore cannot be incorporated into the collagen matrix and is very readily degraded proteolytically. As a consequence of these effects, the total amount of collagen deposited in the extracellular space is decreased.

It is known that inhibition of prolinehydroxylase by known inhibitors, such as $\alpha,\alpha'$-dipyridyl, leads to inhibition of the $C1_q$ biosynthesis of macrophages (W. Müller et al., FEBS Lett. 90 (1978), 218; and Immunbiology 155 (1978) 47). The classical route of complement activation is thereby eliminated. Inhibitors of prolinehydroxylase therefore also act as immunosuppressants, for example in cases of immunity complex diseases.

It is known that prolinehydroxylase is effectively inhibited by pyridine-2,4- and -2,5-dicarboxylic acid (K. Mayamaa et al., Eur. J. Biochem. 138 (1984) 239-245). However, these compounds are effective as inhibitors in the cell culture only in very high concentrations (V. Günzler et al. Collagen and Rel. Research 3, 71, 1983).

DE-A 3,432,094 describes pyridine-2,4- and -2,5-dicarboxylic acid diesters with 1-6 carbon atoms in the ester alkyl part as medicaments for inhibiting prolinehydroxylase and lysinehydroxylase.

However, these lower alkyl diesters have the disadvantage that they are split too rapidly in the organism to give the acids, and do not arrive at their site of action in the cell at a sufficiently high concentration and are thus of little suitability for possible administration as medicaments.

The use of mixed ester/amides, higher alkyl diesters and diamides of pyridine-2,4- and -2,5-dicarboxylic acid for effectively inhibiting collagen biosynthesis in animal models has already been proposed (P 37 03 959.8, P 37 03 962.8 and P 37 03 963.6).

It has now been found, surprisingly, that mixed ester-/amides, higher alkyl diesters and diamides of pyridine-2,4-dicarboxylic acid which carry a further substituent in the 5-position of the pyridine ring are also excellent inhibitors of collagen biosynthesis in animal models.

The mixed ester/amides and higher alkyl diesters proposed to date and the diamides hydrolyze at a faster or slower rate to give pyridine-2,4- or -2,5-dicarboxylic acid, which previous knowledge shows is the actual active substance (see loc. cit. K. Mayama et al.). It is therefore all the more surprising that the substituted pyridine-2,4-dicarboxylic acid derivatives are also excellent inhibitors of collagen biosynthesis in animal models, since these compounds hydrolyze not to give the pure dicarboxylic acids but to give dicarboxylic acids which are substituted in the 5-position.

The invention thus relates to: substituted pyridine-2,4-dicarboxylic acid derivatives of the formula I

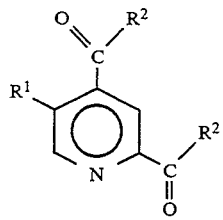

in which:

$R^1$ denotes halogen, carboxyl or $C_1$-$C_4$-alkoxycarbonyl or $R^1$ denotes alkyl, alkenyl or alkynyl with up to 9 C atoms, the radicals mentioned being optionally interrupted by a carbonyl group and the radicals mentioned being optionally mono- or disubstituted by halogen, hydroxyl, nitro, cyano, amino, $C_1$-$C_4$-alkoxy, carboxyl, $C_1$-$C_4$-alkoxycarbonyl, $C_1$-$C_4$-alkylcarbonyloxy or $C_1$-$C_4$-alkyl- or $C_1$-$C_4$-dialkylamino, or optionally substituted by phenyl, naphthyl, thienyl, furyl, pyrrolyl or pyridyl, these aryl or heteroaryl radicals mentioned being in turn optionally monosubstituted by halogen, carboxyl, amino, $C_1$-$C_4$-alkyl or $C_1$-$C_4$-dialkylamino or hydroxyl, or $R^1$ denotes phenyl, naphthyl, thienyl, furyl, pyrrolyl or pyridyl, these aryl or heteroaryl radicals mentioned being in turn optionally monosubstituted by carboxyl, amino, hydroxyl or $C_1$-$C_4$-alkyl- or $C_1$-$C_4$-dialkylamino, or $R^1$ is a substituent of the formula $-OR^3$, or $-N(R^3)_2$, in which $R^3$ is hydrogen or $C_1$-$C_9$-alkyl, $C_1$-$C_9$-alkenyl, $C_1$-$C_9$-alkynyl or $C_1$-$C_9$-alkylcarbonyl, these radicals being optionally mono- or disubstituted by halogen, hydroxyl, nitro, cyano, amino, $C_1$-$C_4$-alkoxy, carboxyl, $C_1$-$C_4$-alkoxycarbonyl, $C_1$-$C_4$-alkylcarbonyloxy or $C_1$-$C_4$-alkyl- or $C_1$-$C_4$-dialkylamino, or optionally substituted by phenyl, naphthyl, thienyl, furyl, pyrrolyl or pyridyl, these aryl or heteroaryl radicals mentioned being in turn optionally monosubstituted by halogen, carboxyl, amino, $C_1$-$C_4$-alkyl- or $C_1$-$C_4$-dialkylamino or hydroxyl, and it also being possible for the two substituents $R^3$ in $-N(R^3)_2$ to differ independently of one another, and $R^2$ denotes a substituent of the formula $-OR^4$ or $N^4R^5$, in which $R^4$ denotes hydrogen or $C_1$-$C_{12}$-alkyl, which is optionally mono- or disubstituted by halogen, hydroxyl, cyano, carboxyl, $C_1$-$C_4$-alkoxy, $C_1$-$C_4$-alkoxycarbonyl, $C_1$-$C_4$-alkylcarbonyloxy, or $C_1$-$C_4$-alkyl- or $C_1$-$C_4$-dialkylamino, or is optionally substituted by phenyl, which is in turn optionally mono-, di- or trisubstituted by halogen, $C_1$-$C_4$-alkyl or $C_1$-$C_4$-alkoxy, it also being possible for the substituents to differ independently of one another in the case of polysubstitution, or R⁴ denotes cyclohexyl, which is optionally benzofused, or R⁴ denotes phenyl, naphthyl, thienyl, furyl, pyrrolyl or pyridyl, the phenyl, naphthyl and pyridyl radicals being optionally mono-, di- or trisubstituted and the thienyl, furyl and pyrrolyl radicals being optionally monosubstituted by halogen, $C_1$-$C_4$-alkyl or $C_1$-$C_4$-alkoxy, it also being possible for the substituents to differ independently of one another in the case of polysubstitution, and R⁵ denotes hydrogen or $C_1$-$C_3$-alkyl, R⁵ in the case of $C_1$-$C_3$-alkyl radicals together with R⁴, which in this case denotes $C_3$-$C_5$-alkyl, optionally forming a heterocyclic saturated 6-membered ring, it also being possible for the heterocyclic 6-membered ring to contain a second nitrogen atom and in turn to be substituted by phenyl or phenyl-$C_1$-$C_3$-alkyl, and it also being possible for the two radicals R² bonded to the pyridine skeleton via the carbonyl group in the 2- and 4-position to differ independently of one another, and it also being possible for all the alkyl radicals mentioned with more than 2 carbon atoms to be branched, and the physiologically tolerated salts, excluding pyridine-2,4,5-tricarboxylic acid, 5-ethylpyridine-2,4-dicarboxylic acid and the compounds in which R¹ is an aminomethyl radical.

Substituted pyridine-2,4-dicarboxylic acid derivatives of the formula I as claimed in claim 1, in which: R¹ denotes halogen or carboxyl, or R¹ denotes $C_1$-$C_4$-alkyl or $C_2$-$C_4$-alkenyl or -alkynyl, the radicals mentioned being optionally interrupted by a carbonyl group and the radicals mentioned being in turn optionally monosubstituted by halogen, hydroxyl, nitro, cyano, amino or carboxyl, or R¹ denotes phenyl, thienyl, furyl or pyrrolyl, the aryl or heteroaryl radicals mentioned being in turn optionally monosubstituted by carboxyl, or R¹ is a substituent of the formula -OR³ or -N(R³)₂, in which R³ is hydrogen, $C_1$-$C_3$-alkylcarbonyl or $C_1$-$C_3$-alkyl, these radicals being in turn optionally substituted by carboxyl, or R³ denotes phenyl, which is in turn optionally parasubstituted by halogen, and it also being possible for the two substituents R³ in —N(R³)₂ to differ independently of one another, and R² denotes a substituent of the formula -OR⁴ or R⁴R⁵, in which R⁴ denotes hydrogen or $C_1$-$C_{12}$-alkyl, which is optionally mono- or disubstituted by halogen, hydroxyl, cyano, carboxyl, $C_1$-$C_4$-alkoxy, $C_1$-$C_4$-alkoxycarbonyl, $C_1$-$C_4$-alkylcarbonyloxy or $C_1$-$C_4$-alkyl- or $C_1$-$C_4$-dialkylamino, or is optionally substituted by phenyl, which is in turn optionally mono-, di- or trisubstituted by halogen, $C_1$-$C_4$-alkyl or $C_1$-$C_4$-alkoxy, it also being possible for the substituents to differ independently of one another in the case of polysubstitution, or R⁴ denotes cyclohexyl, which is optionally benzofused, or R⁴ denotes phenyl, naphthyl, thienyl, furyl, pyrrolyl or pyridyl, the phenyl, naphthyl and pyridyl radicals being optionally mono-, di- or trisubstituted and the thienyl, furyl and pyrrolyl radicals being optionally monosubstituted by halogen, $C_1$-$C_4$-alkyl or $C_1$-$C_4$-alkoxy, it also being possible for the substituents to differ independently of one another in the case of polysubstitution, and R⁵ denotes hydrogen or $C_1$-$C_3$-alkyl, R⁵ in the case of the $C_1$-$C_3$-alkyl radicals together with R⁴, which in this case denotes $C_3$-$C_5$-alkyl, optionally forming a heterocyclic saturated 6-membered ring, it also being possible for the heterocyclic 6-membered ring to contain a second nitrogen atom and to be in turn substituted by phenyl or phenyl-$C_1$-$C_3$-alkyl, and it also being possible for the two radicals R² bonded to the pyridine skeleton via the carbonyl group in the 2- and 4-position to differ independently of one another, and it also being possible for all the alkyl radicals mentioned with more than 2 carbon atoms to be branched, and the physiologically tolerated salts, excluding pyridine-2,4,5-tricarboxylic acid, 5-ethyl-pyridine-2,4-dicarboxylic acid and the compounds in which R¹ is an aminomethyl radical.

Substituted pyridine-2,4-dicarboxylic acid derivatives of the formula I'

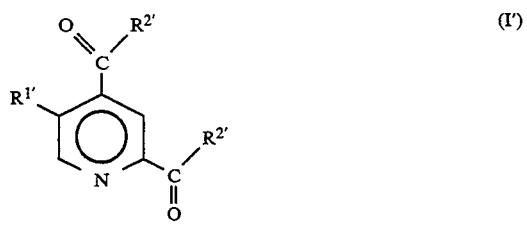

in which the substituents R¹' and R²' have the same meaning as R¹ and R² in formula I as claimed in claim 1, but including pyridine-2,4,5-tricarboxylic acid, 5-ethyl-pyridine-2,4-dicarboxylic acid and the compounds in which R¹' is an aminomethyl radical, for use as medicaments.

Substituted pyridine-2,4-dicarboxylic acid derivatives of the formula I' as claimed in claim 3, in which R¹' and R²' have the same meaning as R¹ and R² in formula I as claimed in claim 2, for use as medicaments.

Halogen is understood as fluorine, chlorine, bromine and iodine, in particular chlorine, bromine and iodine.

In the case of polysubstitution, the substituents can also differ independently of one another.

The invention furthermore relates to a process for the preparation of compounds of the formula I, which comprises either converting a 2,4-dimethyl-5-halogenopyridine first into 2,4,5-trimethylpyridine and oxidizing this is pyridine-2,4,5-tricarboxylic acid, which is converted into the trimethoxycarbonyl compound and then reacted to give tripotassium pyridine-2,4,5-tricarboxylate, or oxidizing a 2,4-dimethyl-5-halogenopyridine to give a compound of the formula (I,1)

in which X denotes halogen and subsequently, if appropriate, a) converting the compound of the formula (I,1) into a compound of the formula (1,2)

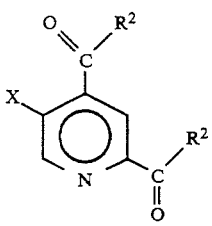

(I,2)

in which X is halogen and $R^2$ has the meanings given in the case of formula I as claimed in claim 1, and, if appropriate, subsequently reacting the compound of the formula (I,2) with a compound of the formula II or II'

$R^6-C\equiv CH$ (II)   $R^6-CH=CH_2$ (II')

in which $R^6$ denotes $C_1$-$C_7$-alkyl, which is optionally mono- or disubstituted by halogen, hydroxyl, nitro, cyano, amino, $C_1$-$C_4$-alkoxy, carboxyl, $C_1$-$C_4$-alkoxycarbonyl or $C_1$-$C_4$-alkyl-or $C_1$-$C_4$-dialkylamino, or is optionally substituted by phenyl, naphthyl, thienyl, furyl, pyrrolyl or pyridyl, these aryl or heteroaryl radicals mentioned being in turn optionally monsubstituted by halogen, carboxyl, amino, $C_1$-$C_4$-alkyl- or $C_1$-$C_4$-dialkylamino or hydroxyl, and in which any free carboxyl groups present are optionally protected, and, if appropriate, hydrogenating the remaining C-C triple or C-C double bond in the fragment which is now bonded to the pyridine skeleton and is derived from the compound of the formula II or II', or if appropriate reacting the compound of the formula (I,2) with a compound of the formula $H_2$-N-$R^3$, in which $R^3$ has the meanings given in the case of formula I in claim 1 and in which any free carboxyl groups present are optionally protected, or, if appropriate, converting the compound of the formula (I,2) into a compound of the formula (I,3)

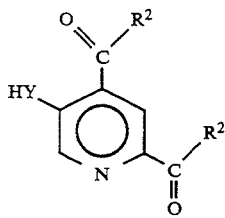

(I,3)

in which Y stands for O or NH and $R^2$ has the meanings given in the case of formula I in claim 1, in a manner which is known per se, and then, if appropriate, reacting the product with a compound of the formula III or III'

$X'-R^3$ (III)

$X'-\overset{O}{\underset{\|}{C}}-R^3$ (III')

in which X' denotes chlorine, bromine or iodine and $R^3$ has the meanings given in the case of formula I in claim 1, and in which any free carboxyl groups present are optionally protected, or, if appropriate, reacting the compound of the formula (I,2) with a compound of the formula IV $R^1$-X' (IV)

in which X' is chlorine, bromine or iodine and $R^1$ has the meanings given in the case of formula I in claim 1, excluding the meanings $-OR^3$ and $-N(R^3)_2$, in which $R^3$ has the meanings given in the case of formula I in claim 1, and in which any free carboxyl groups present are optionally protected, or, if appropriate, reacting the compound of the formula (I,2) with a compound of the formula V $G-Y'-R^3$ (V)

in which

Y' stands for O or $NR^3$,

G stands for an alkali metal and $R^3$ has the meanings given in the case of formula I in claim 1, and in which any free carboxyl groups present are optionally protected, or, if appropriate, b) reacting the compound of the formula (I,1) with a compound of the formula II or II', in which any free carboxyl groups present are optionally protected, and if appropriate then esterifying the carboxylic acids present in the 2- and 4-position of the pyridine skeleton or converting them into the diamides or ester/amides, and if appropriate hydrogenating the remaining C-C triple bond or C-C double bond in the fragment which is now bonded to the pyridine skeleton and is derived from the compound of the formula II or II', or if appropriate reacting the compound of the formula (I,1) with a compound of the formula $H_2$N-$R^3$, in which $R^3$ has the meanings given in the case of formula I in claim 1 and in which any free carboxyl groups present are optionally protected, or if appropriate converting the compound of the formula (I,1) into a compound of the formula (I,4)

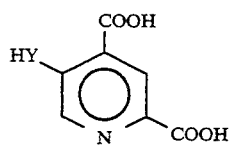

(I,4)

in which Y stands for O or NH, and if appropriate then esterifying the carboxylic acids present in the 2- and 4-position of the pyridine skeleton, or converting them into the diamides or ester/amides, and, if appropriate, subsequently reacting the product with a compound of the formula III or III', in which any free carboxyl groups present are optionally protected, or if appropriate reacting the compound of the formula (I,1) with a compound of the formula IV, in which any free carboxyl groups present are optionally protected and the compounds of the formula $R^3$O-I and $(R^3)_2$N-I, in which $R^3$ has the meanings given in the case of formula I in claim 1, being excluded, or if appropriate reacting the compound of the formula (I,1) with a compound of the formula V, in which any free carboxyl groups present are optionally protected, and if appropriate then esterifying the carboxylic acids optionally present in the 2- and 4-position of the pyridine skeleton in the products obtained according to b), or converting them into the diamides or ester/amides, or, if appropriate, c) first protecting the carboxyl groups present in the 2- and 4-position of the pyridine skeleton in the compound of the formula (I,1) with a protective group, to give a compound of the formula (I,10)

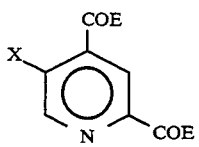
(I,10)

in which E denotes a protective group, and, if appropriate, subsequently reacting the compound of the formula (I,10) with a compound of the formula II or II', in which any free carboxyl groups present are optionally protected, and if appropriate then splitting off the protective groups E of the carboxyl groups in the 2- and 4-position of the pyridine skeleton either selectively or together, and if appropriate esterifying the resulting free carboxylic acids or converting them into the diamides or ester/amides, and if appropriate hydrogenating the remaining C-C triple bond or C-C double bond in the fragment which is now bonded to the pyridine skeleton and is derived from the compound of the formula II or II', or if appropriate reacting the compound of the formula (I,10) with a compound of the formula $H_2N-R^3$, in which $R^3$ has the meanings given in the case of formula I in claim 1 and in which any free carboxyl groups present are optionally protected, or if appropriate converting the compound of the formula (I,10) into a compound of the formula (I,11)

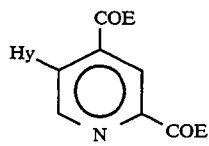
(I,11)

in which Y stands for O or NH, and if appropriate then splitting off the protective groups E of the carboxyl groups in the 2- and 4-position of the pyridine skeleton either selectively or together, and if appropriate esterifying the resulting free carboxylic acids or converting them into the diamides or ester/amides, and if appropriate subsequently reacting the product with a compound of the formula III or III', in which any free carboxyl groups present are optionally protected, or if appropriate reacting the compound of the formula (I,10) with a compound of the formula IV, in which any free carboxyl groups present are optionally protected, the compounds of the formula $R^3O-I$ and $(R^3)_2N-I$ in which $R^3$ has the meanings given in the case of formula I in claim 1 being excluded.

or if appropriate reacting the compound of the formula (I,10) with a compound of the formula V, in which any free carboxyl groups present are optionally protected, and, if appropriate, subsequently splitting off the protective group E of the carboxyl groups in the 2- and 4-position of the pyridine skeleton, either selectively or together, in the products obtained by c), and if approporiate esterifying the resulting free carboxylic acids or converting them into the diamides or ester/amides, and if appropriate subsequently splitting off the protective groups present in the products hydrolytically or hydrogenolytically, and if appropriate converting the compounds obtained according to a), b) or c) into their physiologically tolerated salts.

The preparation of the compounds according to the invention is illustrated in the following synthesis equation.

SYNTHESIS EQUATION

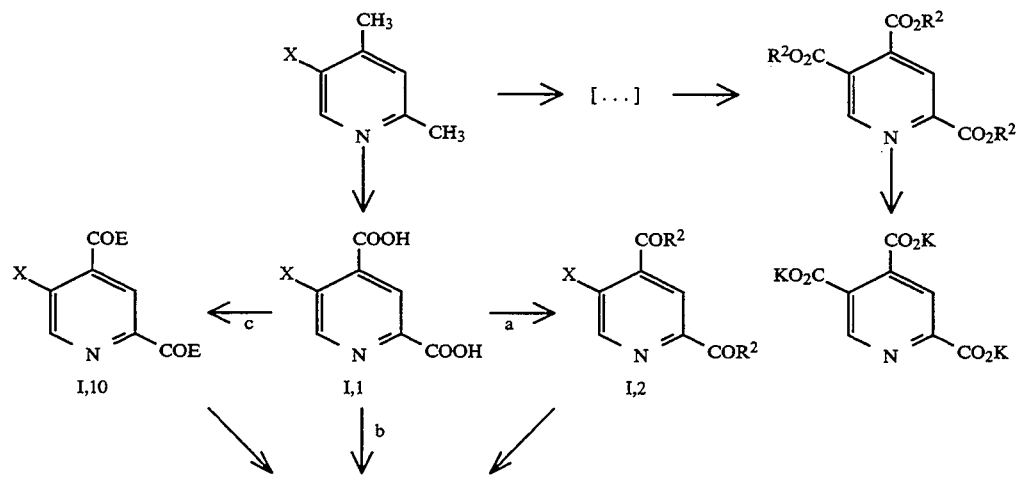

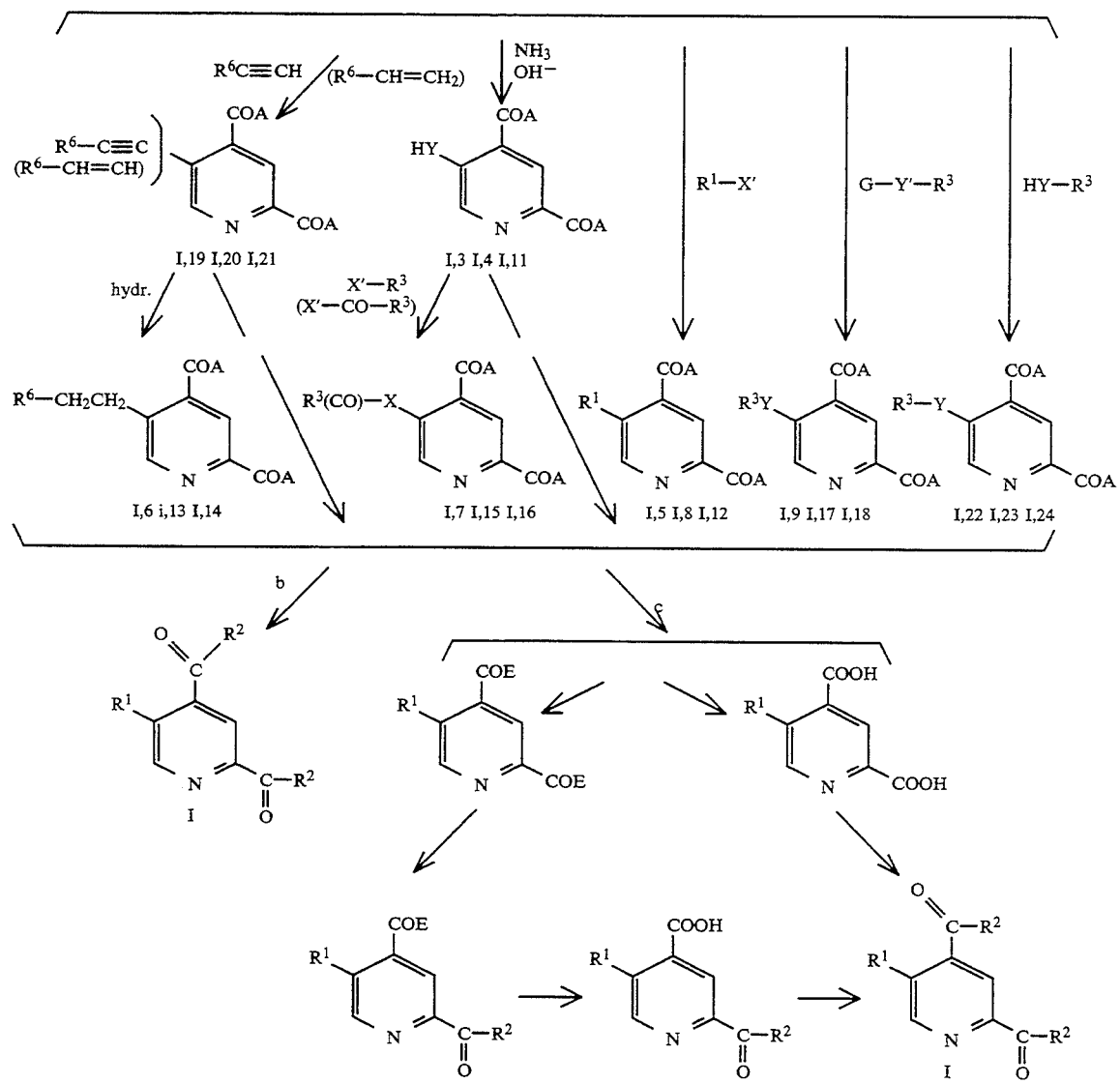

A = OH, R²E
G = alkali metal
X = F, Cl, Br, I
X' = Cl, Br, I
E = protective group
Y = O, NH
Y' = O, NR³

The compounds of the formula (I,1) are obtained, for example, by halogenation of 2,4-dimethylpyridine. The reaction can be carried out in concentrated sulfuric acid or in oleum, preferably with an $SO_3$ content of 25–65%, at temperatures of 40°–80° C. Chlorine, bromine or iodine can be used as the halogenating agent, which is preferably used in an amount of half a mole per mole of 2,4-dimethylpyridine. The reaction time is preferably 1–6 hours. The 5-halogeno-2,4-dimethylpyridine is then oxidized to the compound of the formula (I,1) in the usual oxidizing agents, such as nitric acid, chromic acid, bichromate or potassium permanganate. The solvents are, for example, glacial acetic acid, sulfuric acid or water, the pH preferably being 7–9 if water is used.

Pyridine-2,4,5-tricarboxylic acid can be prepared from the 5-halogeno-2,4-dimethylpyridine by methylation in the 5-position and oxidation, and the product can be converted into the corresponding tripotassium pyridine-2,4,5-tricarboxylate by reaction, for example, with KOH in methanol.

Three different process variants can now be used to prepare further substances according to the invention:

Process variant a)

The compounds of the formula (I,1) are converted into the dicarboxylic acid derivatives of the formula (I,2). The reaction is carried out in a manner analogous to that which has already been proposed for pyridine-2,4- and -2,5-dicarboxylic acids in German Patent Applications P 37 03 959.8, P 37 03 962.8 and P 37 03 963.6. These patent applications are expressly referred to at this point.

Process variant b)

The compounds of the formula (I,1) are used further without prior reaction.

Process variant c)

The two carboxyl groups present in the 2- and 4-position of the pyridine ring in the compounds of the formula (I,1) are protected with a customary carboxyl-protective group (compound (I,10)).

Ester protective groups such as are also used in peptide synthesis are suitable temporary carboxyl-protective groups (compare, for example, Kontakte Merck 3/79, pages 15 and 19 et seq.).

The methyl, benzyl or tert.-butyl esters, and furthermore ONbzl, OMbzl and OPic are frequently used. The protective group is split off by acid or alkaline hydrolysis or by hydrogenation in the presence of a transition metal catalyst, depending on the protective group (Houben-Weyl, Methoden der Organischen Chemie (Methods of Organic Chemistry), Volume E5, pages 496–504, 4th edition, 1985, Georg Thieme Verlag, Stuttgart).

The further reactions of the compounds (I,1), (I,2) or (I,10) are based on replacement of the halogen atom in the 5-position.

Thus, for example, the compound of the formula (I,1), (I,2) or (I,10) can be reacted with a compound of the formula II or II'. The reaction preferably takes place in the presence of a catalyst, such as $((C_6H_5)_3P)_2PdCl_2$ in the simultaneous presence of a base, such as triethylamine, and under simultaneous copper catalysis. The reaction can be carried out without a solvent or in solvents, such as chlorinated hydrocarbons, such as methylene chloride, chloroform or tri- or tetrachloroethylene, or benzene or toluene, at temperatures from room temperature up to the boiling point of the solvent over a reaction time of 30 minutes to 16 hours (see J. Med. Chem. 1987, 30, 185–193).

In the reaction between the alk-(1)-ine derivative or alk(1)-ene derivative and the 5-halogenopyridine-2,4-dicarboxylate, a compound of the formula (I,19), (I,20) or (I,21) which contains a C-C triple bond or C-C double bond is formed and, if appropriate, can then be hydrogenated selectively and/or completely using customary hydrogenating agents, such as $H_2/Pd$. The customary solvents, such as alcohols, in particular methanol, ethanol or isopropanol, are used here.

The compounds of the formula (I,1), (I,2) and (I,10) can likewise be reacted with an amine $H_2N-R^3$, which adds on to the 5-position, hydrogen halide being split off (compounds (I,22), (I,23) and (I,24)). The reaction is preferably carried out in the presence of inert solvents, such as toluene, at the boiling point, preferably at 110°–130° C.

Where they are not commercially available, the amines of the formula $H_2N-R^3$ can be prepared in a simple manner by processes which are known from the literature.

To prepare the pyridine-2,4-dicarboxylic acid derivatives substituted by $-OR^3$ or $-N(R^3)_2$ in the 5-position, the compound (I,1), (I,2) or (I,10) is first converted into the corresponding alcohol or amine ((I,3), (I,4) or (I,11): Y=O or NH). This can be effected, for example, by reaction of the compound (I,1), (I,2) or (I,10) with sodium hydroxide solution or potassium hydroxide solution, which is preferably 1–15N ((I,3), (I,4) and (I,11): Y=O) or with an ammonia solution, the density of which is preferably between 0.7 and 0.89, in an autoclave, preferably at temperatures of 100°–160° C. over reaction times of 1–4 hours ((I,3), (I,4) and (I,10): Y=NH). A catalyst, such as, for example, a copper salt, preferably copper sulfate, can be used for both reactions.

If appropriate, the alcohols or amines formed are then reacted with compounds of the formula III or III' in the subsequent reaction step. If compounds of the formula III or III' which contain free carboxyl groups are used, it is advantageous, before the reaction, for these to be protected with a suitable protective group which can be split off again, if appropriate, when the reaction has ended (see loc. cit. Kontakte Merck, Houben-Weyl, Volume E5).

The two reactants, that is to say the alcohol or the amine of the formula (I,3), (I,4) or (I,11) (Y=O or NH) and the halide of the formula III or III', are mixed in equimolar amounts or with up to about a 5-fold excess of III or III' and the mixture is reacted at temperatures between room temperature and 100° C., preferably between 30° and 60° C., until the reaction has ended. The end of the reaction can be determined by means of thin layer chromatography (TLC control). One variant of this process comprises using a suitable solvent, such as diethyl ether, dimethoxyethane, tetrahydrofuran, chlorinated hydrocarbons, such as methylene chloride, chloroform or tri- or tetrachloroethylene, benzene, toluene or polar solvents, such as dimethylformamide, acetone or dimethylsulfoxide. An excess of halide of the formula III or III' of up to about 5 times the amount can also be used here. The reaction temperatures here are between room temperature and the boiling point of the solvent, temperatures in the range from room temperature to 130° C. being particularly preferred.

If appropriate, the reaction can also be carried out in the presence of bases. Possible additional bases are inorganic acid-trapping agents, such as carbonates or bicarbonates, for example sodium carbonate, potassium carbonate, sodium bicarbonate or potassium bicarbonate, or organic acid-trapping agents, such as tertiary amines, such as triethylamine, tributylamine or ethyl diisopropylamine, or heterocyclic amines, such as N-alkylmorpholine, pyridine, quinoline or dialkylanilines, as well as alkali metal hydrides, such as sodium hydride.

Another possibility of preparing compounds of the formula (I,5), (I,8) or (I,12) according to the invention comprises reacting a compound of the formula (I,1), (I,2) or (I,10) with a substituted or unsubstituted, saturated or mono-unsaturated alkyl halide, preferably iodide or bromide (formula IV). The reaction is preferably carried out in the presence of a strong base, such as butyl-lithium.

One possibility of preparing compounds of the formula (I,9), (I,17) and (I,18) comprises reacting the compounds of the formula (I,1), (I,2) or (I,10) with an alkali metal salt of an alcohol (of the formula V). Methanol, ethanol or isopropanol is preferably used here, and the alkali metal can preferably be sodium or potassium. The reaction is carried out at temperatures between room temperature and the boiling point of the solvent, and the reaction times can be between 10 hours and 100 hours, preferably 60 hours.

According to process variant b)-as described above- the 5-halogeno-pyridine-2,4-dicarboxylic acids are first converted into the compounds (I,5), (I,6), (I,9), (I,19), (I,22), (I,3) or (I,7) and only then, if appropriate in a subsequent reaction step in accordance with the processes which have been described in German Patent Applications P 37 03 959.8, P 37 03 962.8 and P 37 03 063.6, are they converted into products of the formula I according to the invention.

According to process variant c), to prepare further substances according to the invention, if appropriate the carboxyl-protective groups present in the compounds (I,14), (I,16), (I,11), (I,12), (I,21), (I,23) and (I,18) are removed either selectively in succession or together and the compounds are converted into the corresponding $R^2$ derivatives, as has been proposed in German Patent Applications P 37 03 959.8, P 37 03 962.8 and P 37 03 963.6 for pyridine-2,4- and -2,5-dicarboxylic acid diesters/diamides/ester-amides. This opens up the possibility of preparing both symmetrically and unsymmetrically substituted diesters, diamides or ester/amides.

By suitable selection of the protective groups and by suitable selection of the process for splitting off these protective groups, it is furthermore possible for any carboxyl groups present in the substituent $R^1$ and for the carboxyl groups in the 2- and 4-position of the pyridine ring to be esterified with different or-if appropriate-with identical substituents.

Where they are not commercially available, the compounds of the formula II are obtained, for example, from 1,2-dihalides, in particular 1,2-dibromides, after 2-fold dehydrohalogenation, or by reaction of ketones or aldehydes with acetylene and if appropriate subsequent reduction of the alcohol formed. Corresponding methods are described, for example, in Organikum, Organisch chemisches Grundpraktikum (Basic Practical Organic Chemistry), 15th edition, VEB Deutscher Verlag der Wissenschaften, Berlin 1976, page 299 et seq. (from dihalides) and 560 et seq. (ethylation). Substituted alkyne derivatives of the formula II can be prepared, for example, from the corresponding alk-(1)-inols, which can be oxidized by methods which are known from the literature, for example directly, to give carboxylic acids, which if appropriate can be converted into esters or amides. On the other hand, the alk(1)inol can also be converted into a halogen derivative, in particular a chlorine derivative, it being possible for the chlorine atom in turn to be subsequently replaced, for example by a nitrile group, which can in turn be converted into an amine, if appropriate. If desired, this amine can also be oxidized to give the corresponding nitro compounds. The nitrile group can likewise be hydrolyzed to a carboxylic acid, which can then in turn be converted into esters or amides. Disubstituted alkine derivatives of the formula II can also be prepared in an analogous manner. Another method of preparing substituted alkine derivatives of the formula II is nucleophilic substitution of halogen compounds, such as, for example, halogenoalkanes, with sodium acetylide. Corresponding methods are described, for example, in "Reaktionen und Synthesen (Reactions and Syntheses)" in Org.Chem. Praktikum (Practical Organic Chemistry) Tietze/Eicher, Thieme-Verlag, Stuttgart/N.Y. 1981, page 38.

Where they are not commercially available, the alkene compounds of the formula II' can be prepared in a simple manner by processes which are known from the literature.

Where they are not commercially available, the compounds of the formula III, III' and IV can also be synthesized in a simple manner (for example Organikum, Organisch chemisches Grundpraktikum (Basic Practical Organic Chemistry), VEB Deutscher Verlag der Wissenschaften, 15th edition, Berlin 1976; a summary is to be found in the Method Register, page 826: Halogen compounds).

If free carboxyl groups are present in the compounds of the formula III, III' or IV, before the reaction with the compounds of the formula (I,3)/(I,4)/(I,11) or (I,2)-/(I,1)/(I,10), these can be provided, if appropriate, with a suitable protective group (see loc. cit. Kontakte Merck), which can be split off again hydrolytically or hydrogenolytically, if appropriate, when the reaction has ended (see loc. cit. Houben-Weyl, Volume E5).

The compounds of the formula V can be prepared by the customary method by reaction of equimolar amounts of an alkali metal with an alcohol. Here also, any carboxyl groups present can be provided with a temporary protective group (see loc. cit. Kontakte Merck).

If appropriate, working up of the products can be carried out, for example, by extraction or by chromatography, for example over silica gel. The product isolated can be recrystallized and if appropriate reacted with a suitable acid to give a physiologically tolerated salt. Examples of possible suitable acids are: mineral acids, such as hydrochloric and hydrobromic acid, and sulfuric, phosphoric, nitric or perchloric acid, or organic acids, such as formic, acetic, propionic, succinic, glycolic, lactic, malic, tartaric, citric, maleic, fumaric, phenylacetic, benzoic, methanesulfonic, toluenesulfonic, oxalic, 4-aminobenzoic, naphthalene-1,5-disulfonic or ascorbic acid.

The compounds of the formula I and I' according to the invention have useful pharmacological properties, and in particular exhibit activity as inhibitors of prolinehydroxylase and lysinehydroxylase, as fibrosuppressants and as immunosuppressants.

The activity of fibrogenase can be determined by radioimmunological determination of the N-terminal propeptide of collagen type III or of the N- or C-terminal crosslinking domains of collagen type IV (7s-collagen or type IV collagen $NC_1$) in the serum.

For this purpose, the hydroxyproline, procollagen III peptide, 7s-collagen and type IV collagen $NC_1$ concentrations in the liver of a) untreated rats (control)
b) rats who have been given carbon tetrachloride ($CCl_4$ control)
c) rats who have been given first $CCl_4$ and then a compound according to the invention were measured (this test method is described by Rouiller, C., experimental toxic injury of the liver; in The Liver, C. Rouiller, Volume 2, pages 335–476, New York, Academic Press, 1964).

The pharmacological efficacy of the substances according to the invention has been investigated. A clear inhibition of prolinehydroxylase and lysinehydroxylase was thereby found.

The compounds of the formula I and I' can be used as medicaments in the form of pharmaceutical preparations which contain them, if appropriate with tolerated pharmaceutical excipients. The compounds can be used as medicines, for example in the form of pharmaceutical preparations, containing these compounds as mixtures with a pharmaceutical organic or inorganic excipient which is suitable for enteral, percutaneous or parenteral administration, such as, for example, water, gum arabic, gelatin, lactose, starch, magnesium stearate, talc, vegetable oils, polyalkylene glycols, petroleum jelly and the like.

The pharmaceutical preparations can be in solid form, for example as tablets, coated tablets, suppositories or capsules, in semi-solid form, for example as ointments, or in liquid form, for example as solutions, suspensions or emulsions. If appropriate, they are sterilized and/or contain auxiliaries, such as preservatives, stabilizers, wetting agents, emulsifiers, salts for modifying the osmotic pressure or buffers. They can also additionally contain other therapeutically active substances.

The invention is illustrated in more detail below with the aid of examples.

EXAMPLES

Example 1

Preparation of 5-bromo-2,4-dimethylpyridine

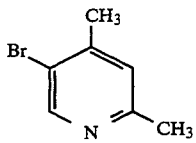

150 ml of 65% strength oleum are added dropwise to 28.9 ml of 2,4-dimethylpyridine, while cooling with ice and stirring, such that the temperature does not rise above 35° C. When the solution has become homogeneous, 6.42 ml of bromine are slowly added dropwise, with stirring. The mixture is stirred at 80° C. for 3½ hours. After cooling, it is carefully added dropwise to 1 kg of ice, neutralized with solid $Na_2CO_3$ and extracted 3 times with 300 ml of ether each time. The organic layer is separated off and dried over magnesium sulfate. After removal of the solvent by distillation in vacuo, 34.6 g of a pale yellow oil consisting of the isomers 5-bromo-2,4-dimethylpyridine and 3-bromo-2,4-dimethylpyridine are obtained. The isomers are separated by column chromatography on silicon dioxide gel to give 10 g of 5-bromo-2,4-dimethylpyridine as a colorless liquid (13.0 g of 3-bromo-2,4-dimethylpyridine). Yield: 22%.

Example 2

Preparation of 5-bromo-2,4-pyridinedicarboxylic acid

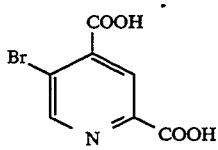

4 g of 5-bromo-2,4-dimethylpyridine from Example 1 are heated to 70°–80° C. in 200 ml of water and 2.4 g of KOH. Half of 12.74 g of potassium permanganate is then introduced in portions. The solution is heated to the boiling point and the remainder of the potassium permanganate is added. The mixture is stirred at 70°–80° C. for 20 hours and then filtered hot with suction and the precipitate is washed 4 times with 50 ml portions of hot water. The combined filtrates are concentrated to 100 ml in vacuo. The solution is brought to pH 1 with concentrated hydrochloric acid and left to stand at 0° C. for 20 hours. The crystalline solid is filtered off with suction and dried at 100° C. in vacuo. The yield is 2.9 g. Melting point 261°–263° C. Yield: 55%.

Example 3

Preparation of dimethyl 5-bromo-2,4-pyridinedicarboxylate (called "dimethyl 5-bromodicarboxylate" below)

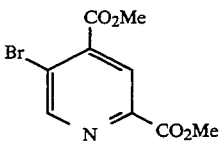

1 g of 5-bromo-2,4-pyridinedicarboxylic acid is dissolved in 20 ml of methanol, and 1 ml of concentrated sulfuric acid is added dropwise. The solution is stirred at 75° C. for 24 hours. It is then cooled, rendered alkaline with saturated sodium bicarbonate solution and extracted with 3 portions of ethyl acetate. The combined organic phases are washed with water and dried with magnesium sulfate and the solvent is removed in vacuo. 1.0 g of a white solid with a melting point of 102°–104° C. remains. Yield: 90%.

Example 4

Preparation of 5-hydroxy-2,4-pyridinedicarboxylic acid

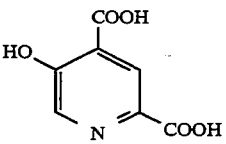

A mixture of 500 mg of 5-bromo-2,4-pyridinedicarboxylic acid from Example 2, 20 ml of 10N aqueous sodium hydroxide solution and 250 mg of copper sulfate is heated at 165° C. in an autoclave for 4 hours. After cooling, the copper salt is filtered off with suction, the pH is brought to 1 with concentrated hydrochloric acid and the solution is evaporated. The solid is heated in a little methanol, the salts are filtered off and the solution is left to stand at 0° C. for 20 hours. The solid which has precipitated out is separated off and dried. Yield: 70 mg Melting point 280°–285° C.

Example 5

Preparation of 5-amino-pyridine-2,4-dicarboxylic acid

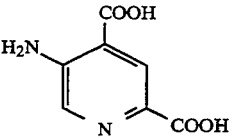

A mixture of 500 mg of 5-bromo-pyridine-2,4-dicarboxylic acid from Example 2, 100 mg of copper sulfate and 20 ml of ammonia solution (d=0.91) is heated at 160° C. in an autoclave for 4 hours. The solution is evaporated to dryness, the solid is heated with a little methanol and the insoluble material is removed from the solution. After 20 hours, a white solid precipitates out at 0° C. and is filtered off and dried. Yield: 70 mg Melting point 315° C. decomposition.

Example 6

Preparation of dimethyl 5-methoxypyridine-2,4-dicarboxylate

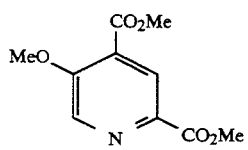

300 mg of dimethyl 5-bromopyridine-2,4-dicarboxylate (from Example 3) are dissolved in 5 ml of absolute methanol, and 120 mg of sodium methylate are added. After 60 hours under reflux, the mixture is poured onto ice and 2 ml of 2N HCl, rendered alkaline with NaHCO$_3$ and extracted with 2 portions of CH$_2$Cl$_2$. After the extract has been dried over MgSO$_4$, the solvent is evaporated. 175 mg of a white solid remain. Melting point: 133°–135° C.

Example 7

Preparation of dimethyl 5-(4-hydroxy-1-butinyl)-pyridine2,4-dicarboxylate

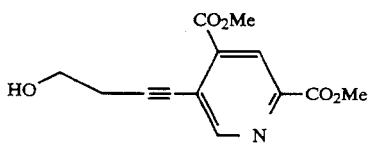

461 mg of dimethyl 5-bromopyridine-2,4-dicarboxylate (from Example 3) and 142 mg of 4-hydroxy-1-butyne are dissolved in methylene chloride in a flask flushed with argon, and 680 μl of triethylamine are added dropwise. The mixture is stirred at room temperature for 15 minutes, 13 mg of ((C$_6$H$_5$)$_3$P)$_2$PdCl$_2$ and 2 mg of CuI are added and the mixture is boiled under reflux for 2 hours. After cooling, the mixture is diluted with methylene chloride and washed with water and sodium chloride solution and the combined organic phases are dried over potassium carbonate. After the solvent has been evaporated off, 347 mg of a white solid remain. Melting point: 87° C.

Example 8

Preparation of dimethyl 5-(3-hydroxy-1-pentinyl)-pyridine-2,4-dicarboxylate

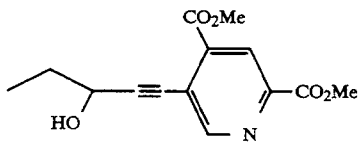

546 mg of dimethyl 5-bromodicarboxylate (from Example 3) and 202 mg of 3-hydroxy-1-pentine are dissolved in methylene chloride in a flask flushed with argon, and 840 μl of triethylamine are added dropwise. The mixture is is stirred at room temperature for 15 minutes, 28 mg of ((C$_6$H$_5$)$_3$P)$_2$ PdCl$_2$ and 4 mg of CuI are added and the mixture is boiled under reflux for 18 hours. After cooling, the mixture is diluted with methylene chloride and washed with water and sodium chloride solution and the combined organic phases are dried over potassium carbonate. After evaporation, 404 mg of a yellow oil which crystallizes at 0° C. remain. Melting point: 65° C.

Example 9

Preparation of dimethyl 5-(4-methoxycarbonyl-1-butinyl)-pyridine-2,4-dicarboxylate

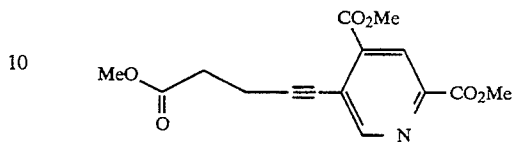

546 mg of dimethyl 5-bromo-dicarboxylate (from Example 3) and 269 mg of methyl 4-pentinoate are dissolved in methylene chloride in a flask flushed with argon, and 840 μl of triethylamine are added dropwise. The mixture is stirred at room temperature for 15 minutes, 28 mg of ((C$_6$H$_5$)$_3$P)$_2$PdCl$_2$ and 4 mg of CuI are added and the mixture is boiled under reflux for 18 hours. After cooling, the mixture is diluted with methylene chloride and washed with water and sodium chloride solution and the combined organic phases are dried over potassium carbonate. After evaporation and chromatography on silica gel, 460 mg of a white solid remain. Melting point: 113° C.

Example 10

Preparation of dimethyl 5-(3-hydroxy-1-propinyl)-pyridine-2,4-dicarboxylate

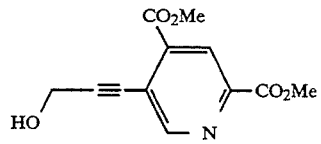

500 mg of dimethyl 5-bromodicarboxylate (from Example 3) and 121 mg of propargyl alcohol are dissolved in methylene chloride in a flask flushed with argon, and 840 μl of triethylamine are added dropwise. The mixture is stirred at room temperature for 15 minutes, 25 mg of ((C$_6$H$_5$)$_3$P)$_2$PdCl$_2$ and 4 mg of CuI are added and the mixture is boiled under reflux for 30 hours. After cooling, the mixture is diluted with methylene chloride and washed with water and sodium chloride solution and the combined organic phases are dried over potassium carbonate. After evaporation and chromatography on silica gel, 260 mg of a white solid remain. Melting point: 104°–106° C.

Example 11

Preparation of dimethyl 5-(5-cyano-1-pentinyl)-pyridine-2,4-dicarboxylate

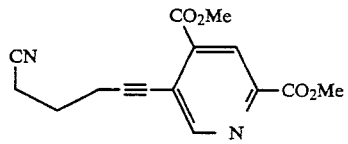

500 mg of dimethyl 5-bromodicarboxylate (from Example 3) and 201 mg of hexinoic acid nitrile are dissolved in a flask flushed with argon, and 840 μl of triethylamine are added dropwise. The mixture is stirred at room temperature for 15 minutes, 25 mg of ((C$_6$H$_5$)$_3$P)$_2$PdCl$_2$ and 4 mg of CuI are added and the mixture is boiled under reflux for 40 hours. After cooling, the mixture is diluted with methylene chloride and washed with water and sodium chloride solution and the combined organic phases are dried over potassium carbonate. After evaporation, 364 mg of a white solid remain. Melting point: 55°–57° C.

Example 12

Preparation of dimethyl 5-(N-benzylamino-1-propinyl)-pyridine-2,4-dicarboxylate

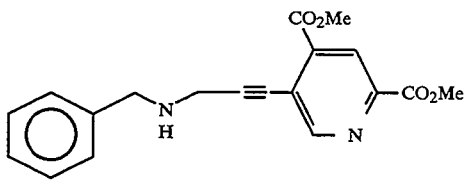

2 g of dimethyl 5-bromodicarboxylate (from Example 3) and 1.25 g of N-benzylpropargylamine are dissolved in methylene chloride in a flask flushed with argon, and 3.4 ml of triethylamine are added dropwise. The mixture is stirred at room temperature for 15 minutes, 25 mg of $((C_6H_5)_3P)_2PdCl_2$ and 4 mg of CuI are added and the mixture is boiled under reflux for 36 hours. After cooling, the mixture is diluted with methylene chloride and washed with water and sodium chloride solution and the combined organic phases are dried over potassium carbonate. After evaporation, 1.25 g of a dark oil which is hydrogenated without purification (Example 18) remain.

Example 13

Preparation of dimethyl 5-(4-hydroxy-butyl)-pyridine-2,4-dicarboxylate

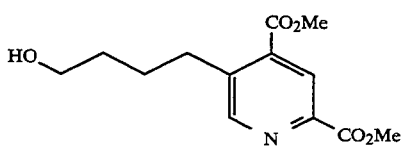

200 mg of dimethyl 5-(4-hydroxy-1-butinyl)-pyridine-2,4-dicarboxylate (from Example 7) are dissolved in 25 ml of methanol and, after addition of the palladium catalyst (10% strength on charcoal) are hydrogenated. The reaction has ended after 4 hours (thin layer control). The catalyst is filtered off and the solution is concentrated in vacuo. The colorless oil is chromatographed on silica gel. Yield: 157 mg Oil

Example 14

Preparation of dimethyl 5-(3-hydroxy-pentyl)-pyridine-2,4-dicarboxylate

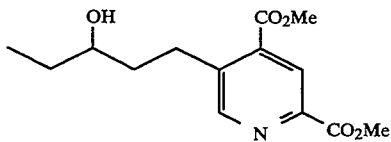

317 mg of dimethyl 5-(3-hydroxy-1-pentinyl)-pyridine-2,4-dicarboxylate (Example 8) are dissolved in 25 ml of methanol and, after addition of the palladium catalyst (10% strength on charcoal) are hydrogenated. The reaction has ended after 4 hours (thin layer control). The catalyst is filtered off and the solution is concentrated in vacuo. The colorless oil is chromatographed on silica gel. Yield: 200 mg Melting point: 77°–78° C.

Example 15

Preparation of dimethyl 5-(4-methoxycarbonyl-butyl)-pyridine-2,4-dicarboxylate

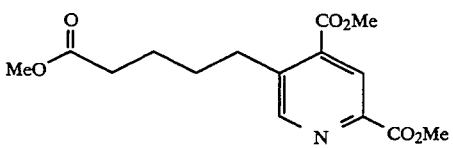

305 mg of dimethyl 5-(4-methoxycarbonyl-1-butinyl)-pyridine-2,4-dicarboxylate (from Example 9) are dissolved in 30 ml of methanol and, after addition of the palladium catalyst (10% strength on charcoal) are hydrogenated. The reaction has ended after 4 hours (thin layer control). The catalyst is filtered off and the solution is evaporated in vacuo. The colorless oil is chromatographed on silica gel. Yield: 260 mg Melting point: 39° C.

Example 16

Preparation of dimethyl 5-(3-hydroxy-propyl)-pyridine-2,4-dicarboxylate

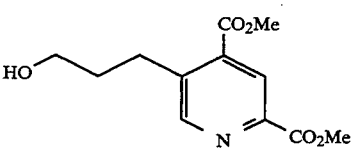

655 mg of dimethyl 5-(3-hydroxy-1-propinyl)-pyridine-2,4-dicarboxylate (Example 10) are dissolved in 50 ml of methanol and, after addition of the palladium catalyst (10% strength on charcoal) are hydrogenated. The reaction has ended after 4 hours (thin layer control). The catalyst is filtered off and the solution is concentrated in vacuo. The colorless oil is chromatographed on silica gel. Yield: 540 mg Melting point: 92°–94° C.

Example 17

Preparation of dimethyl 5-(5-cyano-pentyl)-pyridine-2,4-dicarboxylate

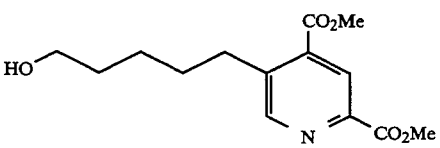

64 mg of dimethyl 5-(5-cyano-1-pentinyl)-pyridine-2,4-dicarboxylate (from Example 11) are dissolved in 25 ml of methanol and, after addition of the palladium catalyst (10% strength on charcoal), are hydrogenated. The reaction has ended after 4 hours (thin layer control). The catalyst is filtered off and the solution is concentrated in vacuo. The colorless oil is chromatographed on silica gel. Yield: 47 mg Oil.

Example 18

Preparation of dimethyl 5-(3-N-benzyl-aminopropyl)-pyridine-2,4-dicarboxylate

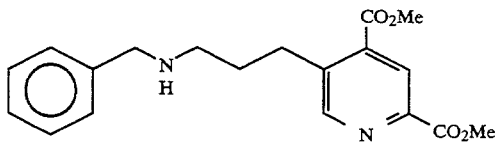

1.25 g of dimethyl 5-(N-benzylamino-1-propinyl)-pyridine-2,4-dicarboxylate (from Example 12) are dissolved in 10 ml of methanol and, after addition of the palladium catalyst (10% strength on charcoal), are hydrogenated. The reaction has ended after 4 hours (thin layer control). The catalyst is filtered off and the solution is concentrated in vacuo. The colorless oil is chromatographed on silica gel. Yield: 1.01 g Oil Example 19

Preparation of diethyl 5-amino-pyridine-2,4-dicarboxylate

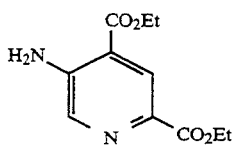

850 mg of 5-amino-pyridine-2,4-dicarboxylic acid (from Example 5) are dissolved in 100 ml of absolute ethanol, 5 ml of concentrated sulfuric acid are added and the mixture is heated under reflux for 20 hours. The solution is concentrated, ethyl acetate and saturated sodium bicarbonate solution are added and the mixture is extracted. The aqueous alkaline phase is extracted 3 times more with ethyl acetate and the combined organic phases are dried over magnesium sulfate and evaporated. 850 mg of a white solid remain. Melting point: 155°–157° C.

Example 20

Preparation of dimethyl 5-(3-chloropropyl)-pyridine-2,4-dicarboxylate

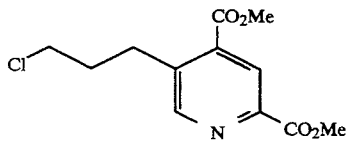

370 mg of dimethyl 5-(3-hydroxypropyl)-pyridine-2,4-dicarboxylate (from Example 16) are dissolved in 10 ml of chloroform, the solution is cooled to 0° C. and 0.18 ml of thionyl chloride in 2 ml of chloroform are slowly added. The mixture is subsequently stirred at room temperature for one hour and then at 60° C. for one hour. After cooling, the mixture is evaporated and the residue is taken up in chloroform and water; the phases are separated and the organic phase is washed with sodium sulfate solution, dried over magnesium sulfate and evaporated. After chromatography on silica gel, 286 mg of a yellow oil remain.

Example 21

Preparation of 3-phenyl-N-([2,4-diethoxycarbonyl]-pyridyl)-propionamide

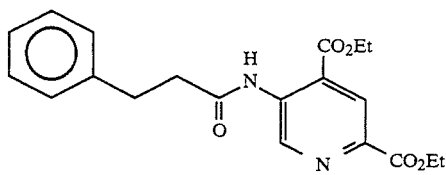

100 mg of diethyl 5-amino-pyridine-2,4-dicarboxylate (from Example 19) are dissolved in 10 ml of tetrahydrofuran, and 20.2 mg of sodium hydride (50% strength suspension in mineral oil) are slowly added, under a nitrogen atmosphere. The mixture is then heated at 60° C. for 1 hour and subsequently cooled and 70.9 mg of 3-phenylpropionyl chloride in 10 ml of tetrahydrofuran are slowly added at 0° C. The solution is boiled for 6 hours and then stirred at room temperature for 16 hours. Water is then added to the mixture at 0° C., the mixture is diluted with ether and the organic phase is separated off. The aqueous phase is extracted again with ether, the combined organic phases are dried over magnesium sulfate and the solvent is stripped off. After chromatography on silica gel, 106 mg of a colorless oil remain.

Example 22

Preparation of dimethyl 5-(3-phenylpropylamino)-pyridine-2,4-dicarboxylate

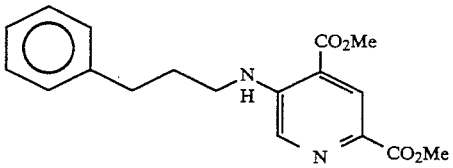

500 mg of dimethyl 5-bromo-pyridine-2,4-dicarboxylate (from Example 3) are dissolved in 10 ml of toluene. 0.26 ml of phenylpropylamine are added dropwise and the mixture is stirred at 120° C. for 10 hours. After cooling, the solvent is evaporated off, the residue is taken up in ethyl acetate and the organic phase is washed with 2 portions each of citric acid, sodium bicarbonate solution and water. After drying over magnesium sulfate, the solvent is evaporated. Chromatography on silica gel gives 117 mg of product with a melting point of 102°–104° C.

Example 23

Preparation of dimethyl 5-(2-methoxycarbonylethenyl)-pyridine-2,4-dicarboxylate

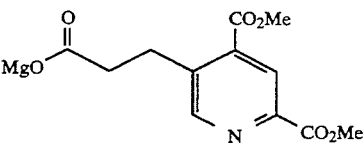

500 mg of dimethyl 5-bromo-pyridine-2,4-dicarboxylate (from Example 3) are heated at 140° C. in an autoclave with 10 ml of methyl acrylate, 0.5 ml of triethylamine, 11 mg of palladium diacetate and 22 mg of triphenylphosphine for 14 hours. After cooling, the mixture is diluted with ethyl acetate, the solid is filtered off and the solvent is evaporated together with the excess methyl acrylate. The product is chromatographed (silica gel) to give 330 mg of a white solid. Melting point: 126°–128° C.

Example 24

Preparation of dimethyl 5-(2-methoxycarbonylethyl)-pyridine-2,4-dicarboxylate

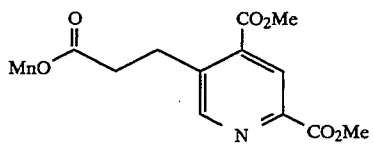

260 mg of dimethyl 5-(2-methoxycarbonyl-ethenyl)-pyridine-2,4-dicarboxylate (from Example 23) are dissolved in 25 ml of methanol and, after addition of the palladium catalyst (10% strength on charcoal), are hydrogenated. The reaction has ended after 4 hours. The catalyst is filtered off and the solution is evaporated in vacuo. The yellow oil is chromatographed (silica gel) and the product crystallizes out. Melting point: 64° C.

We claim:

1. A substituted pyridine-2,4-dicarboxylic acid derivative of the formula I

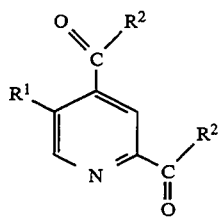

in which:

$R^1$ is a substituent of the formula $-OR^3$, or $-N(R^3)_2$, in which $R^3$ is hydrogen or $C_1$-$C_9$-alkyl, $C_1$-$C_9$-alkenyl, $C_1$-$C_9$-alkynyl or $C_1$-$C_9$-alkylcarbonyl, these radicals being optionally mono- or disubstituted by halogen, hydroxyl, nitro, cyano, amino, $C_1$-$C_4$-alkoxy, carboxyl, $C_1$-$C_4$-alkoxycarbonyl, $C_1$-$C_4$-alkylcarbonyloxy or $C_1$-$C_4$-alkyl- or $C_1$-$C_4$-dialkylamino, or optionally substituted by phenyl, naphthyl, thienyl, furyl, pyrrolyl or pyridyl, these aryl or heteroaryl radicals mentioned being in turn optionally monosubstituted by halogen, carboxyl, amino, $C_1$-$C_4$-alkyl- or $C_1$-$C_4$-dialkylamino or hydroxyl, and it also being possible for the two substituents $R^3$ in $-N(R^3)_2$ to differ independently of one another, and $R^2$ denotes a substituent of the formula -$OR^4$ or -$NR^4R^5$, in which $R^4$ denotes hydrogen or $C_1$-$C_{12}$-alkyl, which is optionally mono- or disubstituted by halogen, hydroxyl, cyano, carboxyl, $C_1$-$C_4$-alkoxy, $C_1$-$C_4$-alkoxycarbonyl, $C_1$-$C_4$-alkylcarbonyloxy, or $C_1$-$C_4$-alkyl- or $C_1$-$C_4$-dialkylamino, or is optionally substituted by phenyl, which is in turn optionally mono-, di- or trisubstituted by halogen, $C_1$-$C_4$-alkyl or $C_1$-$C_4$-alkoxy, it also being possible for the substituents to differ independently of one another in the case of polysubstitution, or $R^4$ denotes cyclohexyl, which is optionally benzofused, or $R^4$ denotes phenyl, naphthyl, thienyl, furyl, pyrrolyl or pyridyl, the phenyl, naphthyl and pyridyl radicals being optionally mono-, di- or trisubstituted and the thienyl, furyl and pyrrolyl radicals being optionally monosubstituted by halogen, $C_1$-$C_4$-alkyl or $C_1$-$C_4$-alkoxy, it also being possible for the substituents to differ independently of one another in the case of polysubstitution, and $R^5$ denotes hydrogen or $C_1$-$C_3$-alkyl, $R^5$ in the case of $C_1$-$C_3$-alkyl radicals together with $R^4$, which in this case denotes $C_1$-$C_5$-alkyl, optionally forming a heterocyclic saturated 6-membered ring, it also being possible for the heterocyclic 6-membered ring to contain a second nitrogen atom and in turn to be substituted by phenyl or phenyl-$C_1$-$C_3$-alkyl, and it also being possible for the two radicals $R^2$ bonded to the pyridine skeleton via the carbonyl group in the 2- and 4-position to differ independently of one another, and it also being possible for all the alkyl radicals mentioned with more than 2 carbon atoms to be branched, or the physiologically tolerated salt, excluding the compounds in which $R^1$ denotes the substituent of the formula $-OR^3$ or $-N(R^3)_2$ and $R^2$ denotes the substituent of the formula $-OR^4$.

2. A pharmaceutical composition comprising an amount effective for use to inhibit prolinehydroxylase or lysinehydroxylase, for use as a fibrosuppressant or immunosuppressant, or for use to influence the metabolism of collagen and collagen-like substances and the biosynthesis of $C1_q$ in the therapy of a mammal of a compound of the formula I'

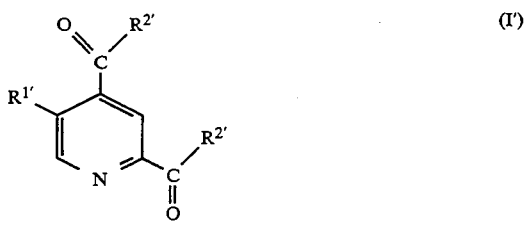

or a physiologically tolerated salt thereof, in which the substituents $R^{1'}$ and $R^{2'}$ have the same meaning as $R^1$ and $R^2$ in formula I as claimed in claim 1, but including pyridine-2,4,5-tricarboxylic acid and its methyl and ethyl esters, together with a pharmaceutically acceptable carrier.

3. A method of inhibiting prolinehydroxylase and lysinehydroxylase in a mammal which comprises administering an effective amount of a compound of the formula I as claimed in claim 1 or a physiologically tolerated salt thereof and including pyridine-2,4,5-tricarboxylic acid and its methyl and ethyl esters or a physiologically tolerated salt thereof.

4. A method for treating a mammal with a fibrosuppressant or immunosuppressant which comprises administering an effective amount of a compound of the formula I as claimed in claim 1 or a physiologically tolerated salt thereof and including pyridine-2,4,5-tricarboxylic acid and its methyl and ethyl esters or a physiologically tolerated salt thereof.

5. A method of influencing the metabolism of collagen and collagen-like substances and the biosynthesis of $C1_q$ in a mammal which comprises administering an effective amount of a compound of the formula I as claimed in claim 1 or a physiologically tolerated salt thereof and including pyridine-2,4,5-tricarboxylic acid and its methyl and ethyl esters or a physiologically tolerated salt thereof.

6. A method of treating disturbances in the metabolism of collagen and collagen-like substances or biosynthesis of $C1_q$ in a mammal which comprises administering an effective amount of a compound of the formula I as claimed in claim 1 or a physiologically tolerated salt thereof and including pyridine-2,4,5-tricarboxylic acid and its methyl and ethyl esters or a physiologically tolerated salt thereof.

7. A substituted pyridine-2,4-dicarboxylic acid derivative of the formula I as claimed in claim 1, in which:

$R^1$ is a substituent of the formula $-OR^3$, or $-N(R^3)_2$, in which $R^3$ is hydrogen or $C_1$-$C_9$-alkyl, $C_1$-$C_9$-alkenyl, $C_1$-$C_9$-alkynyl or $C_1$-$C_9$-alkylcarbonyl, these radicals being optionally mono- or disubstituted by halogen, hydroxyl, nitro, cyano, amino, $C_1$-$C_4$-alkoxy, carboxyl, $C_1$-$C_4$-alkoxycarbonyl, $C_1$-$C_4$-alkylcarbonyloxy or $C_1$-$C_4$-alkyl- or $C_1$-$C_4$-dialkylamino, or optionally substituted by phenyl, naphthyl, thienyl, furyl, pyrrolyl or pyridyl, these aryl or heteroaryl radicals mentioned being in turn optionally monosubstituted by halogen, carboxyl, amino, $C_1$-$C_4$-alkyl-or $C_1$-$C_4$-dialkylamino or hydroxyl, and it also being possible for the two substituents $R^3$ in $-N(R^3)_2$ differ independently of one another.

* * * * *

UNITED STATES PATENT AND TRADEMARK OFFICE
CERTIFICATE OF CORRECTION

PATENT NO. : 5,356,909
DATED : October 18, 1994
INVENTOR(S) : Ekkehard BAADER et al.

It is certified that error appears in the above-indentified patent and that said Letters Patent is hereby corrected as shown below:

On the title page, item [75], change "Dexheim" to --Bad Soden am Taunus--.

Claim 1, Column 24, line 13, change "$C_1-C_3$" to --$C_3-C_5$--.

Claim 7, column 26, PENULTIMATE LINE BEFORE "differ"

insert --to--.

Signed and Sealed this

Second Day of May, 1995

Attest:

BRUCE LEHMAN

Attesting Officer

Commissioner of Patents and Trademarks